(12) United States Patent
Sakazaki et al.

(10) Patent No.: US 11,452,854 B2
(45) Date of Patent: Sep. 27, 2022

(54) METHOD OF MANUFACTURING MICRONEEDLE ARRAY

(71) Applicant: FUJIFILM Corporation, Tokyo (JP)

(72) Inventors: Yoshiki Sakazaki, Kanagawa (JP); Ikuo Takano, Kanagawa (JP); Satoshi Wakamatsu, Kanagawa (JP); Keio Okano, Kanagawa (JP); Kenichiro Tamaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 733 days.

(21) Appl. No.: 16/391,338

(22) Filed: Apr. 23, 2019

(65) Prior Publication Data
US 2019/0351204 A1    Nov. 21, 2019

(30) Foreign Application Priority Data

May 16, 2018 (JP) .............................. JP2018-094789

(51) Int. Cl.
*A61M 37/00* (2006.01)
*B29C 39/10* (2006.01)
(Continued)

(52) U.S. Cl.
CPC ......... *A61M 37/0015* (2013.01); *B29C 39/10* (2013.01); *B29C 39/42* (2013.01); *B29C 39/44* (2013.01); *A61M 2037/0023* (2013.01); *A61M 2037/0046* (2013.01); *A61M 2037/0053* (2013.01); *A61M 2207/10* (2013.01);
(Continued)

(58) Field of Classification Search
CPC ......... B29C 39/10; B29C 39/44; A61M 37/00
See application file for complete search history.

(56) References Cited

U.S. PATENT DOCUMENTS 5,015,097 A    5/1991  Nomoto et al.
10,045,936 B2  8/2018  Mochizuki et al.
(Continued)

FOREIGN PATENT DOCUMENTS

CN    101600957    12/2009
CN    104780967     7/2015
(Continued)

OTHER PUBLICATIONS

"Search Report of Europe Counterpart Application," dated Oct. 15, 2019, pp. 1-9.
(Continued)

*Primary Examiner* — Cachet I Proctor
(74) *Attorney, Agent, or Firm* — JCIPRNET

(57) ABSTRACT

Provided is a method of manufacturing a microneedle array in which an active ingredient is concentrated at a tip while an active ingredient content is guaranteed. In order to achieve the object, a method of manufacturing a microneedle array in which needle-like recessed portions of a mold are filled with a liquid to form one dose of a patch includes determining a filling amount of the liquid from a difference in mass of the mold before and after filling of the liquid, determining a filling state of the liquid in the mold filled with the liquid, sucking the mold in which the filling amount and the filling state of the liquid are determined to be normal from a rear face, and evaporating and drying a solvent of the liquid of the sucked mold.

11 Claims, 13 Drawing Sheets

(51) Int. Cl.
  *B29C 39/42* (2006.01)
  *B29C 39/44* (2006.01)
  *B29K 105/00* (2006.01)
  *B29L 31/00* (2006.01)

(52) U.S. Cl.
  CPC ............... *B29K 2105/0035* (2013.01); *B29K 2105/0073* (2013.01); *B29L 2031/753* (2013.01)

(56) References Cited

U.S. PATENT DOCUMENTS

| | | | |
|---|---|---|---|
| 10,345,098 B2 | 7/2019 | Hu et al. | |
| 10,922,805 B2 | 2/2021 | Murooka et al. | |
| 11,135,413 B2 | 10/2021 | Okano et al. | |
| 2011/0006458 A1* | 1/2011 | Sagi | A61M 37/0015 264/319 |
| 2017/0348880 A1* | 12/2017 | Yamada | B29C 39/24 |
| 2018/0058902 A1 | 3/2018 | Murooka et al. | |
| 2018/0058903 A1 | 3/2018 | Hu et al. | |
| 2018/0066938 A1 | 3/2018 | Hu et al. | |
| 2018/0140815 A1 | 5/2018 | Ono et al. | |
| 2020/0197679 A1 | 6/2020 | Li et al. | |

FOREIGN PATENT DOCUMENTS

| | | | | |
|---|---|---|---|---|
| CN | 105498082 | | 4/2016 | |
| CN | 105498082 A | * | 4/2016 | ............ A61M 37/00 |
| CN | 107405478 | | 11/2017 | |
| CN | 107569767 | | 1/2018 | |
| EP | 2921202 | | 9/2015 | |
| EP | 3235537 | | 10/2017 | |
| EP | 3235537 A1 | * | 10/2017 | ............ A61M 37/00 |
| EP | 3270120 | | 1/2018 | |
| EP | 3270120 A1 | * | 1/2018 | ............ A61M 37/00 |
| JP | 2004106399 | | 4/2004 | |
| JP | 2008124306 | | 5/2008 | |
| JP | 2011224332 | | 11/2011 | |
| JP | 2012200572 | | 10/2012 | |
| JP | 2013153866 | | 8/2013 | |
| JP | 2013153866 A | * | 8/2013 | ........ A61M 37/0015 |
| JP | 2013162982 | | 8/2013 | |
| JP | 2016112169 | | 6/2016 | |
| JP | 2016166769 | | 9/2016 | |
| JP | 2016170164 | | 9/2016 | |
| JP | 2018038509 | | 3/2018 | |
| WO | 2017119715 | | 7/2017 | |
| WO | 2017183441 | | 10/2017 | |

OTHER PUBLICATIONS

Office Action of Japan Counterpart Application, with English translation thereof, dated May 28, 2021, pp. 1-8.
"Office Action of Japan Counterpart Application", dated Mar. 9, 2022, with English translation thereof, p. 1-p. 27.
"Office Action of China Counterpart Application" with English translation thereof, dated Mar. 9, 2022, p. 1-p. 27.

* cited by examiner

FIG. 7
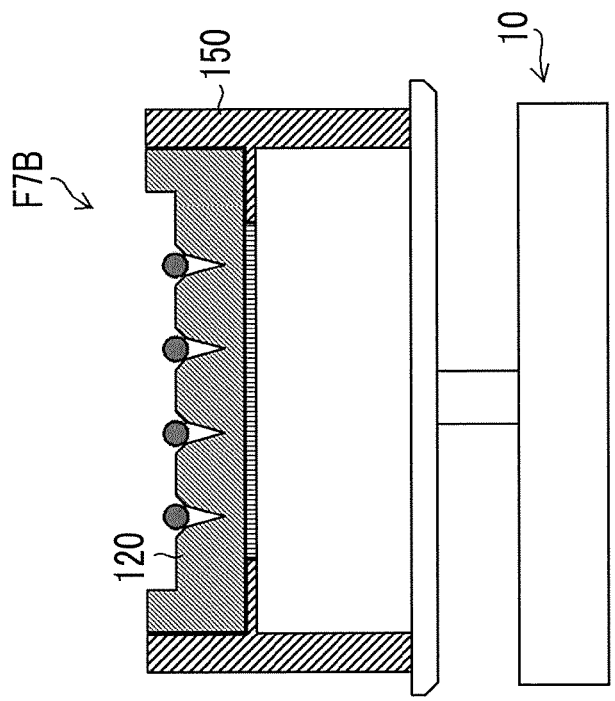
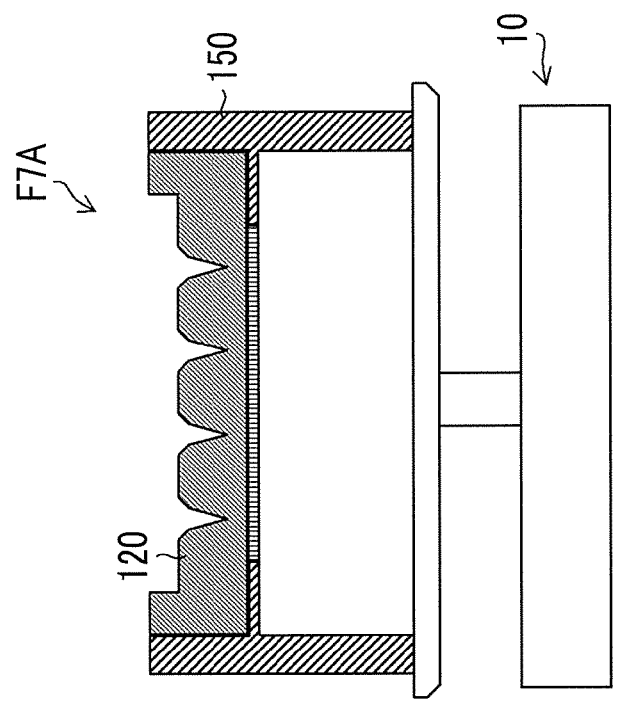

FIG. 11
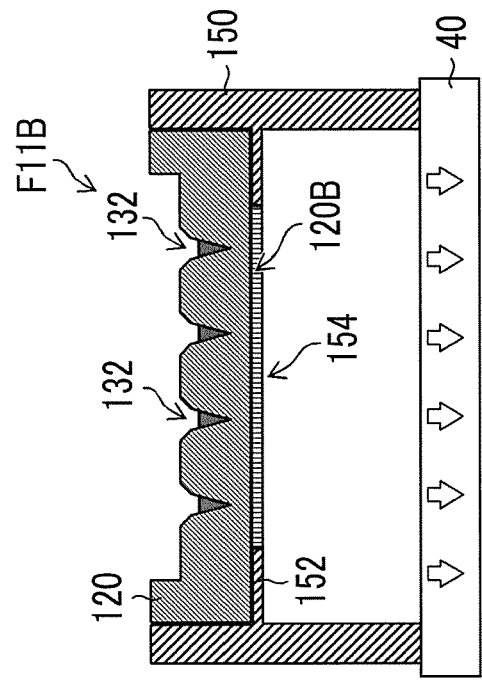
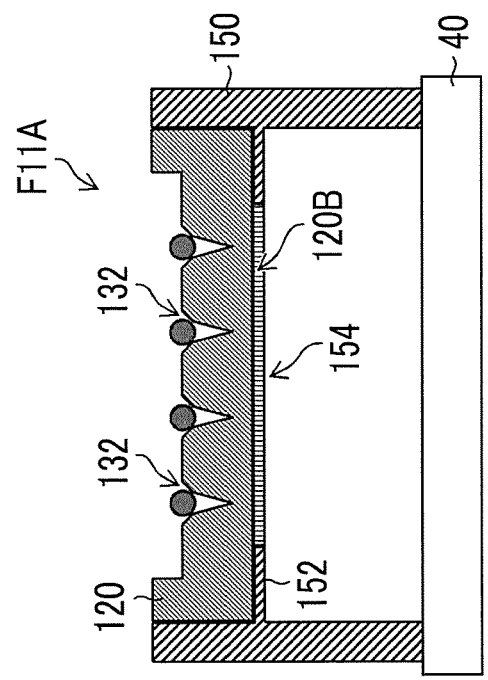

FIG. 16
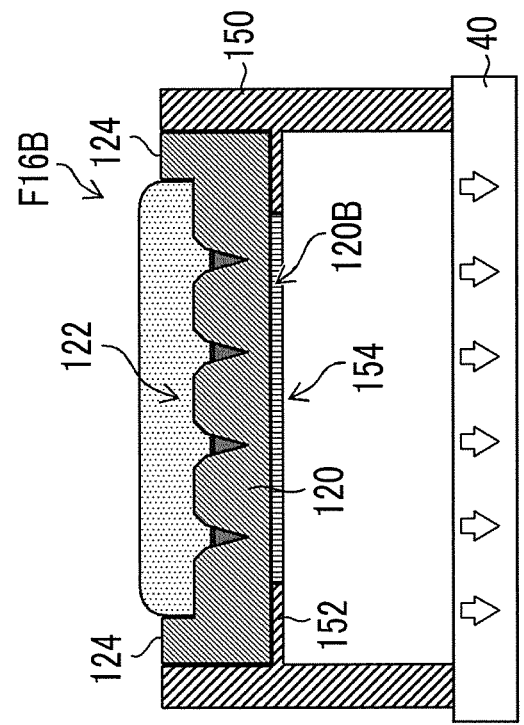
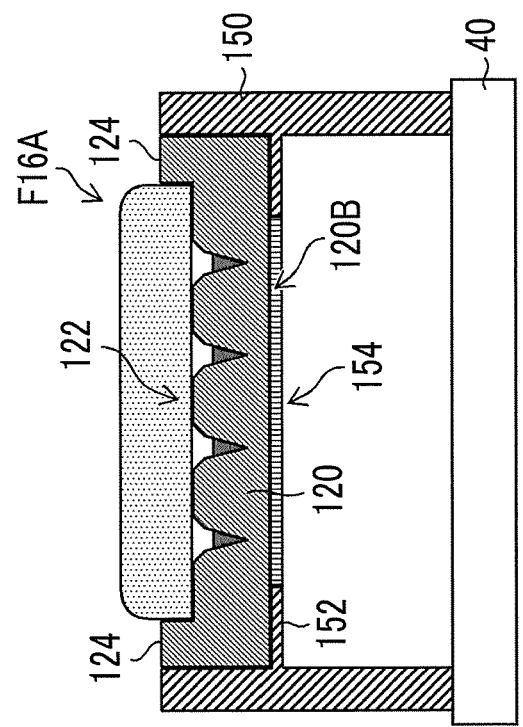

METHOD OF MANUFACTURING MICRONEEDLE ARRAY

CROSS-REFERENCE TO RELATED APPLICATION

The present application claims priority under 35 U.S.C § 119(a) to Japanese Patent Application No. 2018-094789 filed on May 16, 2018, which is hereby expressly incorporated by reference, in its entirety, into the present application.

BACKGROUND OF THE INVENTION

1. Field of the Invention

The present invention relates to a method of manufacturing a microneedle array, and particularly, to a method of manufacturing a microneedle array in which needle-like protruding portions are formed by drying a liquid filling needle-like recessed portions of a mold.

2. Description of the Related Art

In recent years, microneedle arrays (percutaneous absorption sheets) in which needle-like protruding portions (also referred to as fine needles or microneedles) containing a drug are formed have been used to transmit the drug into a skin. Generally, a microneedle array is pushed against a skin to insert needle-like protruding portions into the skin, and thus the drug of the needle-like protruding portions is transmitted into the skin.

As a method of manufacturing a microneedle array, a method has been known in which a mold in which needle-like recessed portions (also referred to as needle hole portions) having an inverted shape of a needle-like protruding portion are formed is used to fill the needle-like recessed portions with a solution containing a drug (also referred to as a drug solution), the solution is dried, and then a solution containing a raw material for needle (also referred to as a needle) is applied and dried to form microneedles.

In microneedle arrays, it is desirable to concentrate an active ingredient of a drug at a tip of a needle-like protruding portion in order to efficiently administer the drug to a patient. JP2011-224332A discloses a technique of continuously decreasing the concentration of a drug from a tip toward a base of a needle-like protruding portion.

The active ingredient content of a drug of a microneedle array is required to be strictly controlled. Therefore, it is necessary to quantify the amount of the drug solution contained in the microneedle array in microneedle array manufacturing steps. JP2011-224332A discloses a technique of dissolving a microneedle array in water to measure the drug content of the microneedle array.

SUMMARY OF THE INVENTION

However, in the method described in JP2011-224332A, it is necessary to perform destructive measurement. Accordingly, it was impossible to guarantee the active ingredient content of a microneedle array to be shipped.

The invention is contrived in view of such circumstances, and an object thereof is to provide a method of manufacturing a microneedle array in which an active ingredient is concentrated at a tip while an active ingredient content is guaranteed.

In order the achieve the object, an aspect of a method of manufacturing a microneedle array is a method of manufacturing a microneedle array in which a plurality of needle-like recessed portions of a surface of a mold are filled with a liquid to form one dose of a patch having a plurality of needle-like protruding portions on a surface thereof, comprising: a pre-filling measurement step of measuring a mass of the mold; a filling step of filling the needle-like recessed portions of the mold whose mass is measured with the liquid; a post-filling measurement step of measuring a mass of the mold filled with the liquid; a filling amount determination step of determining a filling amount of the liquid from a difference in mass of the mold before and after the filling of the liquid; a filling state determination step of determining a filling state of the liquid in the mold filled with the liquid; a suction step of sucking the mold in which the filling amount and the filling state of the liquid are determined to be normal from a rear face; and an evaporation and drying step of evaporating and drying a solvent of the liquid of the sucked mold.

According to this aspect, since the filling amount of the liquid in the mold can be guaranteed, an active ingredient content of the microneedle array can be guaranteed. In addition, since tips of the needle-like recessed portions of the mold can be filled with the liquid, it is possible to concentrate an active ingredient at tips of the needle-like protruding portions of the microneedle array.

It is preferable that in the filling amount determination step, the filling amount is determined to be normal in a case where the difference is within a certain range. Accordingly, it is possible to appropriately determine whether the filling amount of the liquid is normal.

It is preferable that the liquid is a drug solution containing a drug, and in the filling step, a position of the mold is made to coincide with a position of a drug solution jetting nozzle, and the drug solution is jetted from the drug solution jetting nozzle to be landed in the needle-like recessed portions. Accordingly, it is possible to appropriately fill the needle-like recessed portions with the drug solution, and to concentrate the active ingredient at the tips.

It is preferable that the filling step includes a step of imaging a plurality of positions in the mold, and a step of calculating positions of the needle-like recessed portions based on the imaged plurality of positions. Accordingly, it is possible to appropriately make the position of the mold to coincide with the position of the drug solution jetting nozzle.

It is preferable that in the filling state determination step, a captured image of the mold filled with the liquid is analyzed, and the filling state of the drug solution is determined to be normal in a case where the drug solution lands in all the needle-like recessed portions of the mold. Accordingly, it is possible to appropriately determine the filling state of the drug solution.

It is preferable that the liquid is a base solution, and in the filling step, a position of the mold is made to coincide with a position of a base solution spotting nozzle, and the needle-like recessed portion in which the drug solution filling the recessed portion is evaporated and dried is filled with the base solution by spotting. Accordingly, it is possible to appropriately fill the needle-like recessed portion with the base solution.

It is preferable that the mold has a thick bank portion at a peripheral portion thereof, and in the filling state determination step, a captured image of the mold after the filling of the base solution is analyzed, and the filling state of the base solution is determined to be normal in a case where the base solution exists only in a region surrounded by the bank portion. Accordingly, it is possible to appropriately determine the filling state of the base solution.

It is preferable that the post-filling measurement step is performed before the filling state determination step. Accordingly, it is possible to appropriately determine the filling amount of the liquid by reducing the influence of the evaporation of the liquid.

It is preferable that the mold is placed on a conveying tool, and in the pre-filling measurement step and the post-filling measurement step, a mass of the conveying tool and the mold is measured. Accordingly, handling of each step is facilitated, and thus it is possible to appropriately measure the mass in the pre-filling measurement step and the post-filling measurement step.

It is preferable that the conveying tool is provided with adsorption holes in a seating face on which the mold is placed. Accordingly, it is possible to appropriately suck the mold placed on the conveying tool in the suction step.

It is preferable that the mold has gas permeability. Accordingly, it is possible to appropriately suck the mold in the suction step.

According to this aspect, it is possible to concentrate an active ingredient at a tip while guaranteeing an active ingredient content.

BRIEF DESCRIPTION OF THE DRAWINGS

FIG. 7 is a schematic diagram showing a pre-drug solution filling measurement step and a post-drug solution filling measurement step.

FIG. 11 is a schematic diagram showing a first suction step.

FIG. 16 is a schematic diagram showing a second suction step.

DESCRIPTION OF THE PREFERRED EMBODIMENTS

Figure 1:
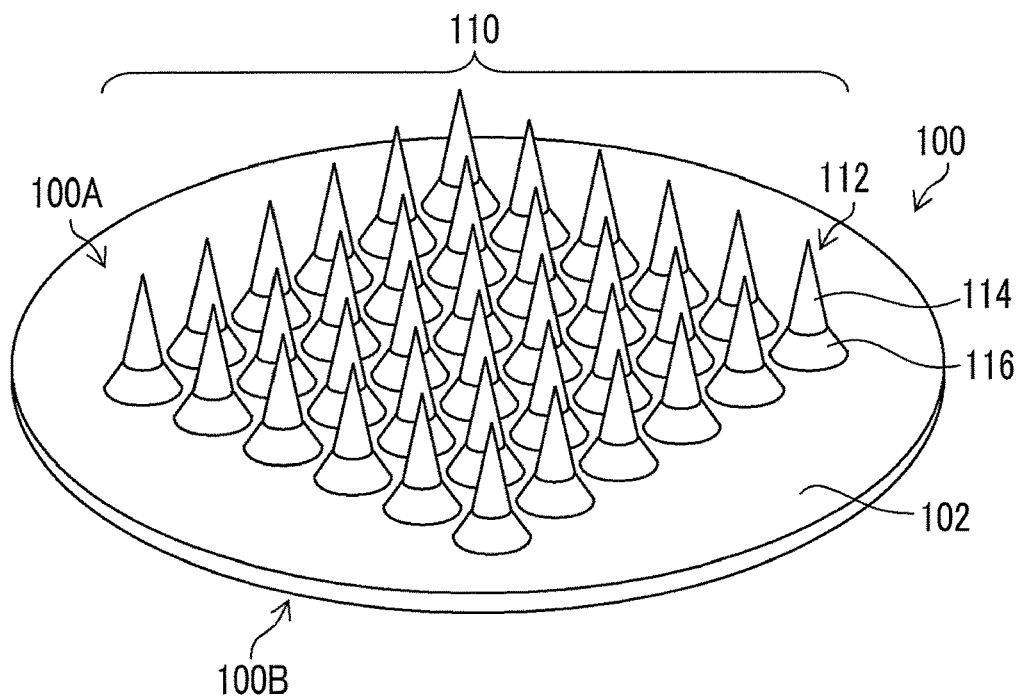
FIG. 1 is a perspective view showing an example of a percutaneous absorption sheet.

Hereinafter, preferred embodiments of the invention will be described with reference to the accompanying drawings. The invention will be described by the following preferred embodiments. Modifications can be made by a number of methods without departing from the scope of the invention, and embodiments other than this embodiment can be utilized. Accordingly, all modifications within the scope of the invention are included in the scope of claims.

In the drawings, the parts indicated by the same symbols are similar elements having similar functions. In this specification, in a case where a numerical value range is expressed using "to", the numerical value range includes the upper limit value and the lower limit value indicated by "to".

Configuration of Percutaneous Absorption Sheet

First, an example of a microneedle array (percutaneous absorption sheet) manufactured by a method of manufacturing a microneedle array according to this embodiment will be described.

FIG. 1 is a perspective view showing an example of a percutaneous absorption sheet 100. The percutaneous absorption sheet 100 according to this embodiment corresponds to a one-dose patch. The percutaneous absorption sheet 100 has a front face (front surface) 100A and a rear face 100B, and is formed of a sheet-like sheet portion 102 and a protrusion pattern 110.

The term "sheet-like" means a thin flat shape as a whole with respect to the front face 100A and the rear face 100B which are two opposed faces having a large area, and the front face 100A and the rear face 100B are not required to be completely flat. In addition, although the sheet portion 102 shown in FIG. 1 has a circular shape in plan view, it may have a rectangular, polygonal, or elliptical shape. The sheet portion may have a circular shape with a D-cut or a notch.

The protrusion pattern 110 has a plurality of needle-like protruding portions 112. The needle-like protruding portions 112 are provided on the front face 100A. The needle-like protruding portion 112 is formed of a needle portion 114 and a frustum portion 116 which connects the needle portion 114 and the sheet portion 102.

A plurality of frustum portions 116 are disposed on the front face 100A of the percutaneous absorption sheet 100. The frustum portion 116 has a three-dimensional structure having two bottom faces and surrounded by a conical face. A large-area one (lower bottom face) of the two bottom faces of the frustum portion 116 is connected to the sheet portion 102. A small-area one (upper bottom face) of the two bottom faces of the frustum portion 116 is connected to the needle portion 114. That is, among the two bottom faces of the frustum portion 116, the bottom face in a direction away from the sheet portion 102 has a small area.

The needle portion 114 has such a shape that a bottom face has a large area and a tip separated from the bottom face has the smallest area. Since the large-area bottom face of the needle portion 114 is connected to the upper bottom face of the frustum portion 116, the needle portion 114 has a tapered shape in a direction away from the frustum portion 116. Therefore, the needle-like protruding portion 112 formed of the needle portion 114 and the frustum portion 116 has a tapered shape as a whole from the sheet portion 102 toward the tip. 4 to 2,500 needle-like protruding portions 112 are provided on the sheet portion 102. However, the number of the needle-like protruding portions is not limited thereto.

In FIG. 1, the frustum portion 116 has a truncated conical shape, and the needle portion 114 has a conical shape. The shape of the tip of the needle portion 114 can be appropriately changed to a curved surface having a curvature radius of 0.01 μm to 50 μm, a flat surface, or the like according to the degree of insertion of the needle portion 114 into a skin.

Configuration of Mold

Figure 2:
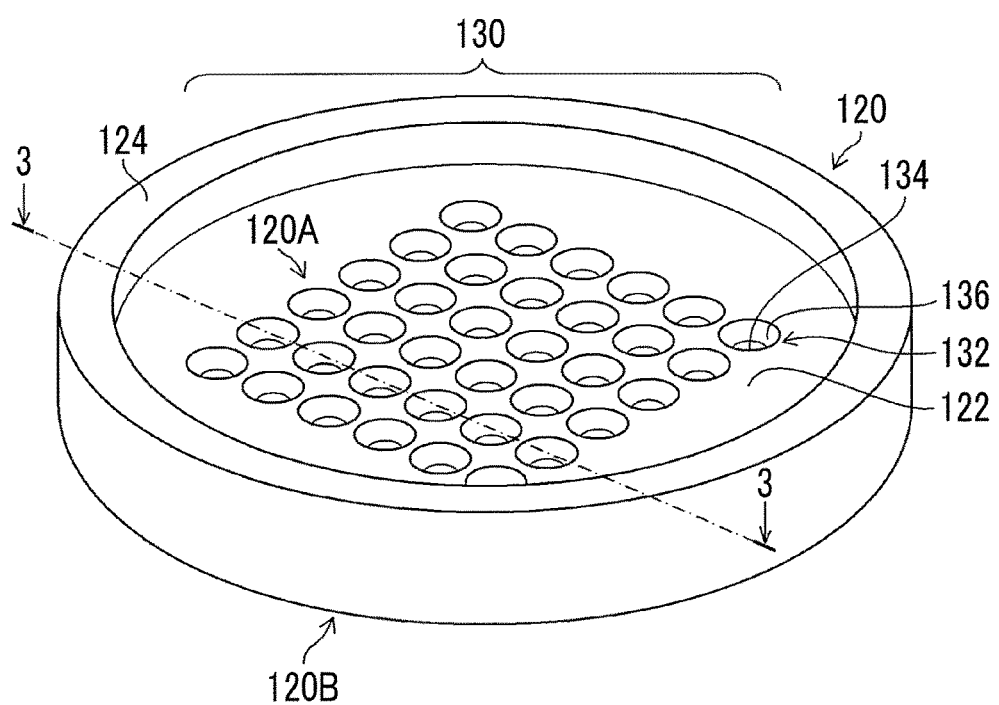
FIG. 2 is a perspective view showing an example of a mold.
Figure 3:
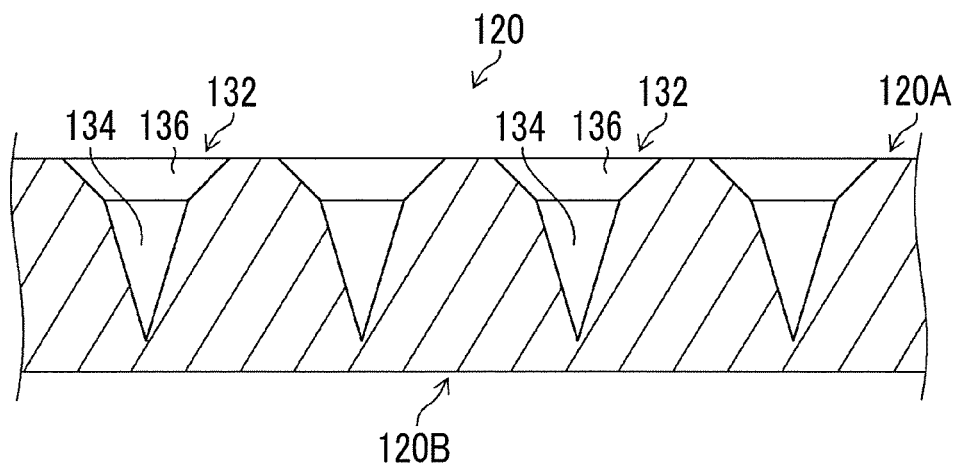
FIG. 3 is a partially enlarged view of a cross section taken along the line 3-3 in FIG. 2.

FIG. 2 is a perspective view showing an example of a mold 120 for manufacturing (molding) the percutaneous absorption sheet 100. FIG. 3 is a partially enlarged view of a cross section taken along the line 3-3 in FIG. 2. The mold 120 has a front face (front surface) 120A and a rear face 120B, and is formed of a flat portion 122, a bank portion 124, and a recess pattern 130.

The flat portion 122 has a flat shape corresponding to the sheet portion 102 of the percutaneous absorption sheet 100. The bank portion 124 is erected at a peripheral portion of the front face 120A and surrounds the flat portion 122. Since the rear face 120B is flat, the bank portion 124 is thicker than the flat portion 122 in the mold 120.

The recess pattern 130 is formed of a plurality of needle-like recessed portions 132 provided in the flat portion 122. The needle-like recessed portion 132 has a shape corresponding to the needle-like protruding portion 112 of the percutaneous absorption sheet 100, and is formed of a tip recessed portion 134 corresponding to the needle portion 114 and a cup portion 136 corresponding to the frustum portion 116.

The tip recessed portion 134 has a tapered shape in a depth direction (thickness direction) of the mold 120. The tip recessed portion 134 may have a diameter of 10 μm to 150 μm and a height of 150 μm to 2,000 μm. The cup portion 136 has an opening in the front face 120A of the mold 120, has a shape which narrows in the depth direction of the mold 120, and is connected to the tip recessed portion 134 at a narrowest portion thereof. The cup portion 136 may have a diameter of 500 μm to 1,000 μm and a height of 100 μm to 500 μm.

The shape of the needle-like recessed portion 132 is not limited to the above example. The needle-like recessed portion may have a shape in which an intermediate recessed portion such as a cylinder, a quadrangular prism, or a polygonal prism having a constant width in the depth direction is provided between the tip recessed portion 134 and the cup portion 136. A through-hole penetrating the mold 120 and reaching the rear face 120B may be formed at the tapered tip. The arrangement, the pitch, the number, and the like of the needle-like recessed portions 132 may be determined by the arrangement, the pitch, the number, and the like of the needle-like protruding portions 112 necessary for the percutaneous absorption sheet 100.

An elastic material or a metal material can be used as a material used for the mold 120. Among these, an elastic material is preferable, and a material having high gas permeability is more preferable.

The oxygen permeability which is representative gas permeability is preferably greater than $1 \times 10^{-12}$ (mL/s·m·Pa), and more preferably greater than $1 \times 10^{-10}$ (mL/s·m·Pa). By producing the mold 120 with a material having high gas permeability, it is possible to suck the liquid filling the needle-like recessed portion 132 by suction from the rear face 120B of the mold 120, and thus it is possible to promote the filling of the needle-like recessed portion 132. In addition, the air existing in the needle-like recessed portion 132 can be removed from the rear face 120B. Accordingly, it is possible to manufacture a percutaneous absorption sheet 100 with fewer defects.

Specific examples of such a material include those obtained by melting or dissolving in a solvent general engineering plastics such as a silicone resin (for example, SYLGARD 184 (registered trademark) manufactured by Dow Corning Corporation or 1310ST manufactured by Shin-Etsu Chemical Co., Ltd.), an ultraviolet curable resin, a polystyrene resin, a polymethyl methacrylate resin, an epoxy resin, a polyethylene terephthalate resin, a polyoxymethylene resin, a polytetrafluoroethylene resin, a polyethylene resin, a phenolic resin, and a urethane resin.

Among these, silicone rubber-based materials can be preferably used since these have durability to transfer resulting from repeated pressurization and have excellent permeability from a material.

Method of Manufacturing Percutaneous Absorption Sheet

Figure 4:
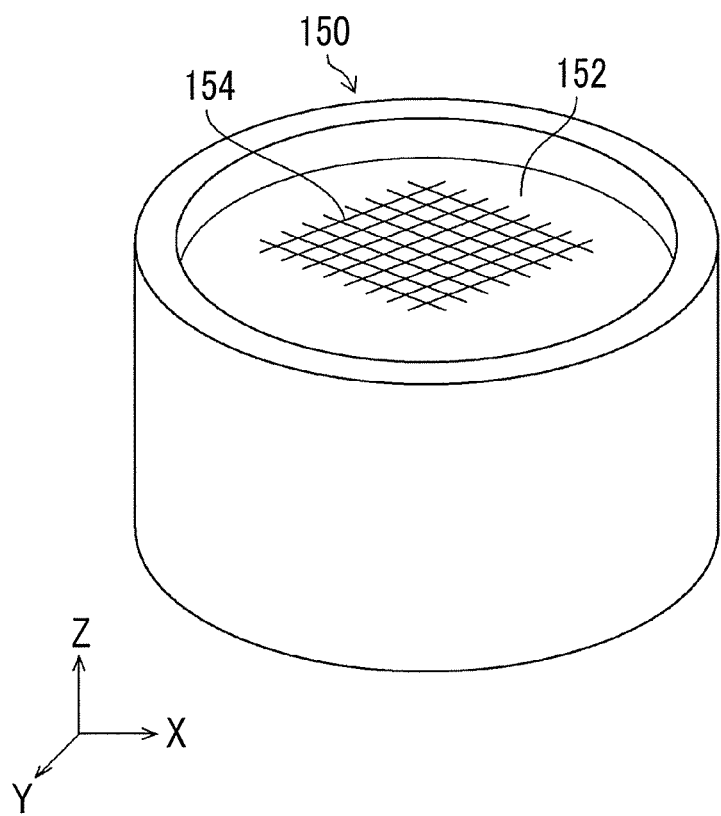
FIG. 4 is a perspective view of a conveying tool.

FIG. 4 is a perspective view of a conveying tool 150 for handling the percutaneous absorption sheet 100. The conveying tool 150 has a seating face 152 on which the percutaneous absorption sheet 100 is placed. In the seating face 152, a mesh-like ventilation portion 154 (an example of adsorption holes) is formed at least at a position corresponding to the recess pattern 130 of the mold 120. The conveying tool 150 is made of plastic such as polypropylene. In addition, it may be made of an inorganic material such as a metal or ceramics. In a case where a metal is used, SUS316L is preferably used in consideration of corrosion resistance.

Figure 5:
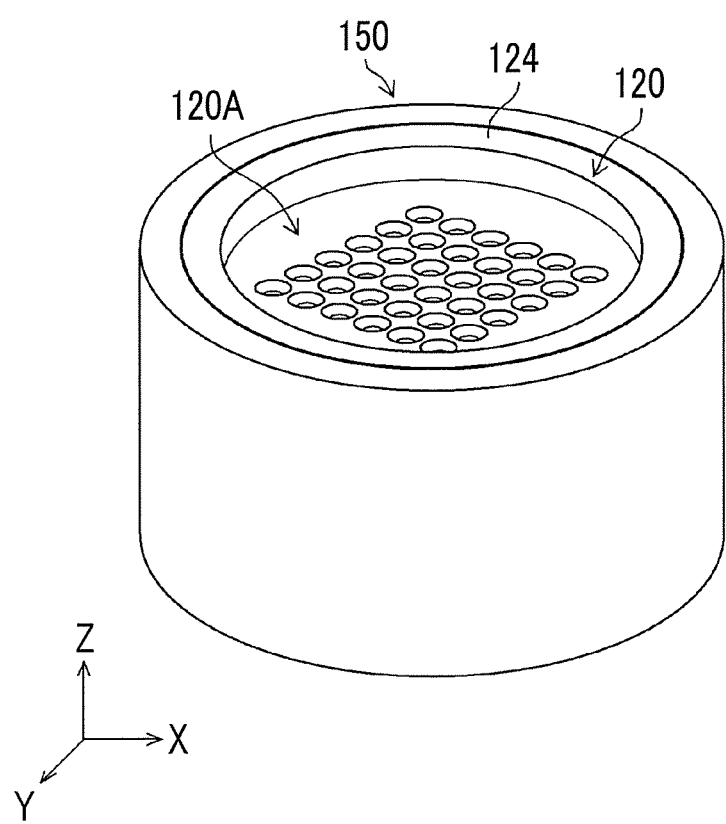
FIG. 5 is a perspective view showing a state in which the mold is mounted on the conveying tool.

FIG. 5 is a perspective view showing a state in which the mold 120 is mounted on the conveying tool 150. The mold 120 is placed on the seating face 152 of the conveying tool 150 with the front face 120A directed upward in a Z direction which is a vertical direction. The conveying tool 150 supports the mold 120 in a state in which the sheet portion 102 of the mold 120 is parallel to an XY plane which is a horizontal surface. In this state, the holes of the ventilation portion 154 of the seating face 152 are preferably disposed directly below the plurality of needle-like recessed portions 132.

Figure 6:
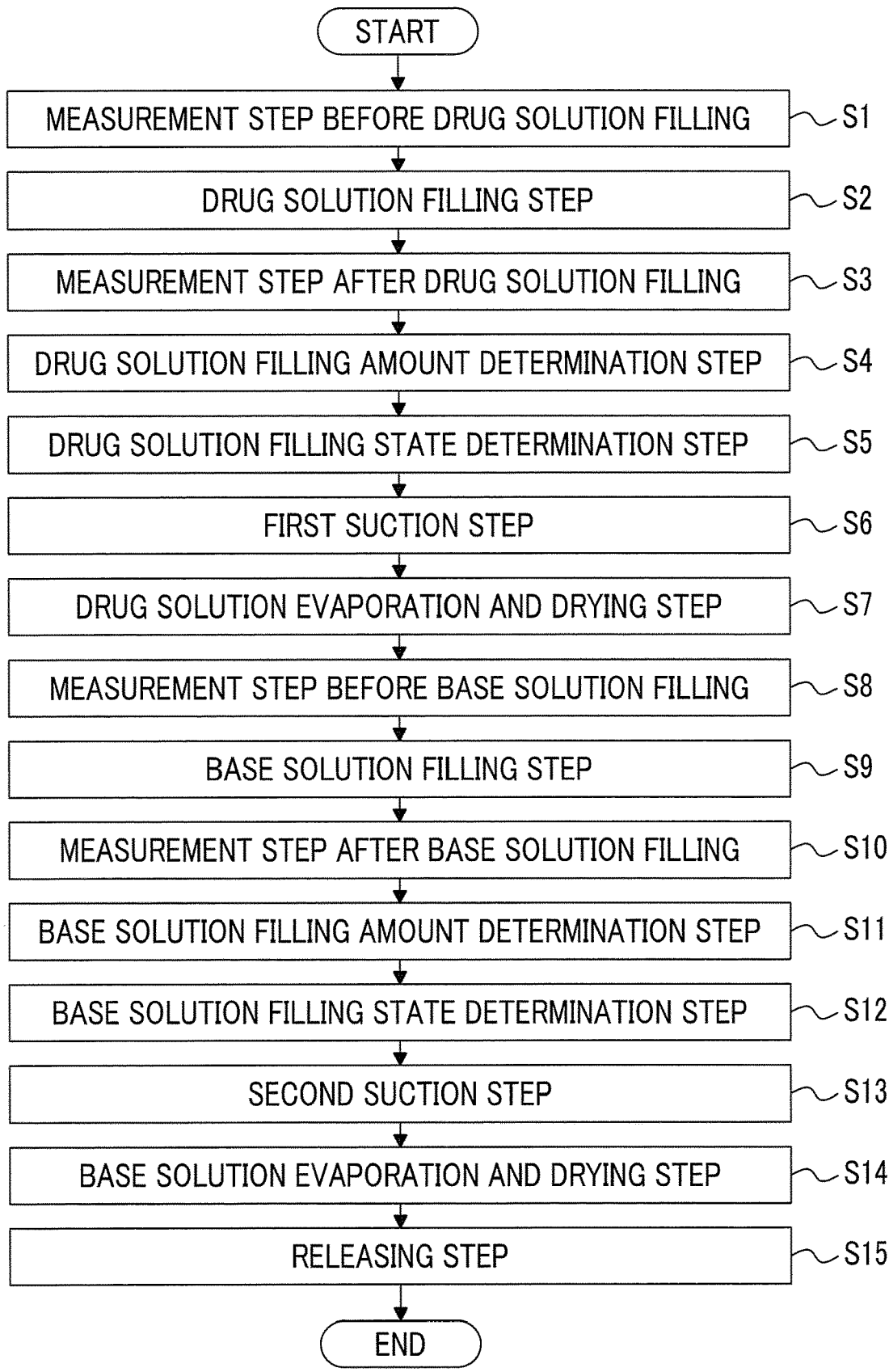
FIG. 6 is a flowchart showing steps of a method of manufacturing the percutaneous absorption sheet.

FIG. 6 is a flowchart showing steps of a method of manufacturing the percutaneous absorption sheet 100. The method of manufacturing the percutaneous absorption sheet 100 includes a pre-drug solution filling measurement step (Step S1) of measuring the mass of the mold 120 before a drug solution filling step, the drug solution filling step (Step S2) of filling the needle-like recessed portions 132 of the mold 120 with a drug solution (an example of a liquid), a post-drug solution filling measurement step (Step S3) of measuring the mass of the mold 120 filled with the drug solution, a drug solution filling amount determination step (Step S4) of determining the filling amount of the drug solution from a difference in mass of the mold 120 before and after the filling of the drug solution, a drug solution filling state determination step (Step S5) of determining the filling state of the drug solution in the mold 120 filled with the drug solution, a first suction step (Step S6) of sucking the mold 120 in which the filling amount and the filling state of the drug solution are determined to be normal from the rear face 120B, and a drug solution evaporation and drying step (Step S7) of drying and evaporating a solvent of the drug solution of the mold 120 sucked from the rear face 120B.

The method of manufacturing the percutaneous absorption sheet 100 further includes a pre-base solution filling measurement step (Step S8) of measuring the mass of the mold 120 before a base solution filling step, the base solution filling step (Step S9) of filling the needle-like recessed portions 132 of the mold 120 with a base solution, a post-base solution filling measurement step (Step S10) of measuring the mass of the mold 120 filled with the base solution, a base solution filling amount determination step (Step S11) of determining the filling amount of the base solution from a difference in mass of the mold 120 before and after the filling of the base solution, a base solution filling state determination step (Step S12) of determining the filling state of the base solution in the mold 120 filled with the base solution, a second suction step (Step S13) of sucking the mold 120 in which the filling amount and the filling state of the base solution are determined to be normal from the rear face 120B, a base solution evaporation and drying step (Step S14) of drying and evaporating a solvent of the base solution of the mold 120 sucked from the rear face 120B, and a releasing step (Step S15) of releasing the percutaneous absorption sheet 100 formed through the base solution evaporation and drying step from the mold 120.

Pre-Drug Solution Filling Measurement Step (Step S1)

In the pre-drug solution filling measurement step, the mass of the mold 120 before the drug solution filling step is measured. FIG. 7 is a schematic diagram showing the pre-drug solution filling measurement step and the post-drug solution filling measurement step. As shown in FIG. 7, an electronic balance 10 is used in the pre-drug solution filling measurement step and the post-drug solution filling measurement step. The electronic balance 10 is, for example, an electromagnetic type or load cell type electronic balance.

As shown in F7A of FIG. 7, in the pre-drug solution filling measurement step, a mass $W_{1B}$ of the mold 120 including the mass of the conveying tool 150 is measured in a state in which the mold 120 is mounted on the conveying tool 150. The measuring instrument which measures the mass of the mold 120 is not limited to the electronic balance, and may be a measuring instrument which can achieve both the measurable range and the resolution.

Drug Solution Filling Step (Step S2)

In the drug solution filling step, the needle-like recessed portions 132 of the mold 120 are filled with the drug solution while position adjustment is performed. The drug solution contains an undiluted drug solution as a medicine (active ingredient), saccharides, additives, and the like. The drug solution further contains water, ethanol, or the like as a solvent.

Figure 8:
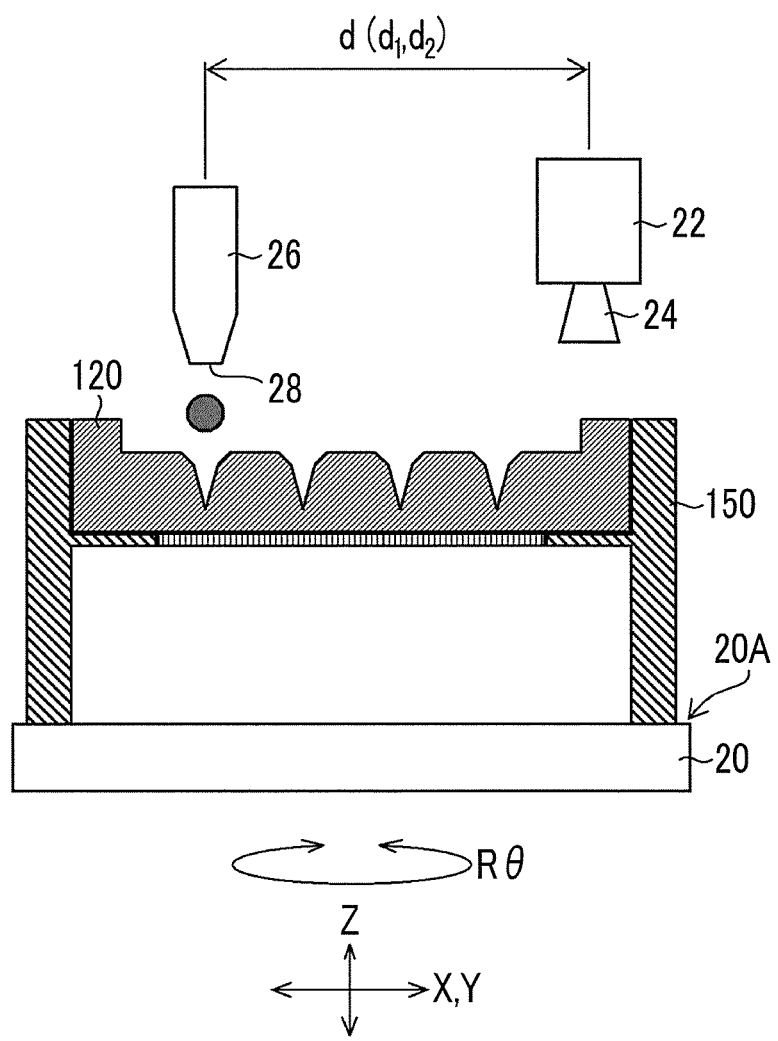
FIG. 8 is a schematic diagram showing a drug solution filling step.

FIG. 8 is a schematic diagram showing the drug solution filling step. In the drug solution filling step, an XY stage 20, a camera 22, a drug solution jetting head 26, and the like are used.

The XY stage 20 has a placing face 20A parallel to the XY plane. The XY stage 20 is provided to be movable in two directions parallel to the XY plane, that is, the X direction and the Y direction orthogonal to the X direction, by a motor (not shown). The XY stage 20 may have a rotation mechanism θ axis having an axis in a direction perpendicular to a surface of the XY stage, or an Rθ stage may be used instead of the XY stage. Depending on the arrangement of the needle-like recessed portions 132 such as a case where the needle-like recessed portions 132 of the mold 120 are arranged in spirals, it may be possible to reduce the filling time in a case where an acceleration/deceleration time in the X direction and the Y direction is omitted and the θ axis is rotated.

The conveying tool 150 is placed on the placing face 20A of the XY stage 20. In the conveying tool 150, the mold 120 is mounted on the seating face 152. Accordingly, the mold 120 is moved in each direction as the XY stage 20 is moved in the X direction or the Y direction.

The camera 22 is provided with, in addition to an imaging lens 24, an imaging element, an analog-to-digital conversion portion, and an image processing circuit (not shown).

The imaging lens 24 is a lens group including a zoom lens, a focus lens, and the like, and makes incident light from a subject incident on the imaging element.

The imaging element is an imaging element of a charge coupled device (CCD) type or a complementary metal oxide semiconductor (CMOS) type in which a large number of light-receiving elements are two-dimensionally arranged on an imaging surface (not shown). The imaging element is disposed at a rear stage of the optical path of the incident light of the imaging lens 24.

The imaging lens 24 images incident light on the imaging surface of the imaging element. The imaging element outputs an analog imaging signal corresponding to the amount of received light. The imaging signal is converted into a digital signal by the analog-to-digital conversion portion, and then generated as an image signal by the image processing circuit.

The camera 22 is disposed above the XY stage 20 in the Z direction, and the imaging lens 24 is directed downward in the Z direction. Therefore, the camera 22 can image the mold 120 placed on the XY stage 20.

The drug solution jetting head 26 is disposed above the XY stage 20 in the Z direction at a position separated from the camera 22 by a distance d in the XY plane consisting of a distance $d_1$ in the X direction and a distance $d_2$ in the Y direction. The drug solution jetting head 26 is provided with a nozzle 28 (an example of a drug solution jetting nozzle) which jets drug solution droplets. Here, the nozzle 28 is directed downward in the Z direction. Although the drug solution jetting head 26 shown in FIG. 8 is provided with one nozzle 28, it may have a plurality of nozzles 28.

As the drug solution jetting head 26, an ink jet head such as a solenoid type ink jet head or a piezo type ink jet head can be used. The amount of one liquid droplet jetted from the nozzle 28 is about 1 to 150 nL.

The drug solution jetted from the nozzle 28 flies downward in the Z direction and lands in the mold 120. Accordingly, the position of the nozzle 28 in the XY plane is equal to the position of the mold 120 in which the drug solution is landed in the XY plane.

Details of Drug Solution Filling Step

Figure 9:
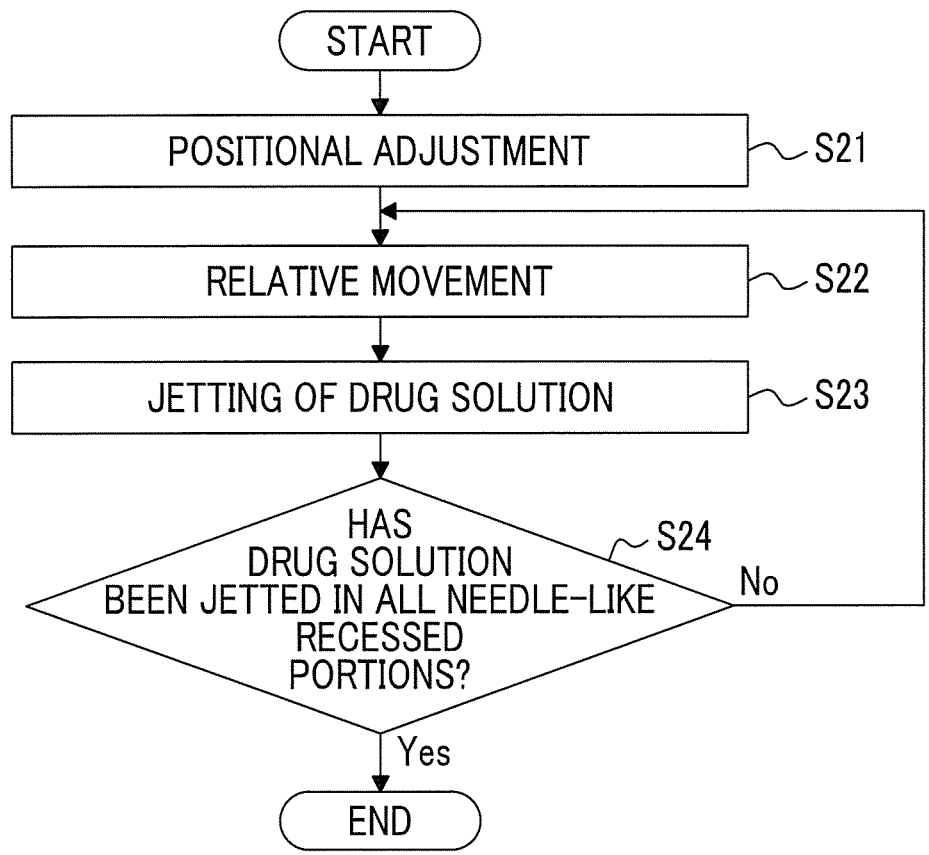
FIG. 9 is a flowchart showing details of the drug solution filling step.

FIG. 9 is a flowchart showing details of the drug solution filling step. The drug solution filling step includes a positional adjustment step (Step S21), a moving step (Step S22), a drug solution jetting step (Step S23), and a jetting completion determination step (Step S24).

Positional Adjustment Step (Step S21)

In the positional adjustment step, positional adjustment is performed such that the position of the needle-like recessed portion 132 of the mold 120 placed on the XY stage 20 in the XY plane coincides with the position of the nozzle 28 of the drug solution jetting head 26 in the XY plane. The position of the needle-like recessed portion 132 may coincide with the position of the nozzle 28 such that the drug solution jetted from the nozzle 28 toward the needle-like recessed portion 132 lands in the needle-like recessed portion 132, and both the positions do not need to strictly coincide. Here, by detecting the position of the needle-like recessed portion 132 from a captured image, the needle-like recessed portion 132 and the nozzle 28 are virtually positioned.

First, the conveying tool 150 on which the mold 120 is mounted is placed on the placing face 20A of the XY stage 20.

Next, the mold 120 is moved by the XY stage 20 within the angle of view of an image captured by the camera 22. Next, the camera 22 images an image of the mold 120. The image of the mold 120 captured by the camera 22 is analyzed to calculate the position of each needle-like recessed portion 132.

For example, the needle-like recessed portion 132 of the mold 120 is moved to a center within the angle of view of an image captured by the camera 22 by the XY stage 20 to detect the XY plane coordinates (X, Y) of the XY stage 20 at that time. By performing this operation on all the needle-like recessed portions 132, the positions of all the needle-like recessed portions 132 can be detected.

In the image of the mold 120 captured by the camera 22, the flat portion 122 has relatively high brightness, and the needle-like recessed portion 132 has relatively low brightness. Using this contrast, the needle-like recessed portion 132 can be moved to the center within the angle of view of the image captured by the camera 22.

All the needle-like recessed portions 132 may not be moved to the center within the angle of view of the image captured by the camera 22. Only the XY plane coordinates (X, Y) of the three to five needle-like recessed portions 132 may be detected, and the orientation (rotation) of the mold 120 in the XY plane, the displacement of the mold 120 in the XY plane, and the expansion and contraction of the mold 120 may be analyzed from the coordinates to detect the positions of other needle-like recessed portions 132.

A plurality of alignment marks may be provided on the mold 120 and read to detect the XY plane coordinates (X, Y) of each needle-like recessed portion 132.

By detecting the position of the needle-like recessed portion 132 with the XY plane coordinates (X, Y) of the XY stage 20, the needle-like recessed portion 132 and the nozzle 28 are virtually positioned.

The positional adjustment may be mechanically performed. For example, the bottom face of the conveying tool 150 may have a D-cut shape, and the XY stage 20 may be provided with a member fitted to the D-cut shape of the conveying tool 150. In addition, the bottom face of the conveying tool 150 may have a rectangular shape or a polygonal shape, and the XY stage 20 may be provided with a member fitted to a corner portion of the conveying tool 150. The orientation of the conveying tool 150 and the mold 120 mounted on the conveying tool 150 may be uniquely determined.

Moving Step (Step S22)

In the moving step, the XY stage 20 is controlled based on the result of the positional adjustment to move the mold 120 in the X direction and the Y direction, and the positions of the drug solution jetting head 26 and the mold 120 are thus adjusted to make the position of the nozzle 28 of the drug solution jetting head 26 in the XY plane and the position of the needle-like recessed portion 132 in the XY plane to coincide. That is, the position of the nozzle 28 is made to coincide with the position of the needle-like recessed portion 132 in plan view from a direction (Z direction) parallel to the drug solution jetting direction of the nozzle 28.

Coordinates (X+$d_1$, Y+$d_2$) obtained by adding the distance $d_1$ in the X direction and the distance $d_2$ in the Y direction between the camera 22 and the nozzle 28 of the drug solution jetting head 26 to the coordinates (X, Y) of the needle-like recessed portion 132 calculated in the positional adjustment step are the coordinates of the nozzle 28. By moving the XY stage 20 to the above coordinates, the position of the nozzle 28 can be made to coincide with the position of the needle-like recessed portion 132.

The distance between the nozzle 28 and the mold 120 is preferably adjusted to 0.1 mm to 10 mm, and more preferably adjusted to 1 mm to 4 mm.

Here, the XY stage 20 is moved. However, the drug solution jetting head 26 may be moved. In a case where the drug solution jetting head 26 is moved, the meniscus of the nozzle 28 may be changed, and this may adversely affect the jetting of the drug solution. Therefore, the XY stage 20 is preferably moved.

Drug Solution Jetting Step (Step S23)

In the drug solution jetting step, the drug solution is jetted from the nozzle 28 of the drug solution jetting head 26. The jetted drug solution lands in the needle-like recessed portion 132. Here, one drug solution droplet is jetted from the nozzle 28 to one needle-like recessed portion 132 and landed in the needle-like recessed portion 132. A plurality of drug solution droplets may be landed in one needle-like recessed portion 132.

Here, the drug solution is jetted from the nozzle 28 after the mold 120 is moved by the XY stage 20. However, the moving step and the drug solution jetting step may be simultaneously performed to jet the drug solution from the nozzle 28 while moving the mold 120 by the XY stage 20.

Jetting Completion Determination Step (Step S24)

In the jetting completion determination step, it is determined whether the drug solution has been jetted and landed in all the needle-like recessed portions 132 of the mold 120. Here, the number of times of jetting of the drug solution in the drug solution jetting step and the number of the needle-like recessed portions 132 whose the position has been detected in the positional adjustment step are compared for determination.

In a case where it is determined that there are needle-like recessed portions 132 in which no drug solution has been landed, the process returns to Step S22 and the same process is performed. That is, the position of the needle-like recessed portion 132 in which no drug solution has been jetted in the XY plane is made to coincide with the position of the nozzle 28 in the XY plane (Step S22), and the drug solution is jetted from the nozzle 28 and landed in the needle-like recessed portion 132 (Step S23). The order of jetting of the drug solution to the needle-like recessed portion 132 is not particularly limited. However, from the viewpoint of reducing a total moving distance of the XY stage 20, jetting is preferably sequentially performed from a needle-like recessed portion 132 disposed at an end of the mold 120 to an adjacent needle-like recessed portion 132.

A method may be used in which a model of the overall arrangement of the needle-like recessed portions 132 is detected, and according to the detected model, jetting is performed with a jetting arrangement pattern prepared in advance. Accordingly, the jetting completion determination step is not required.

In a case where it is determined that the drug solution has been landed in all the needle-like recessed portions 132, the drug solution filling step is completed.

Here, the distance $d_1$ and the distance $d_2$ are treated as known values. However, in a case where the distances are unknown, these can be obtained as follows.

A dummy mold having no needle-like recessed portions 132 is mounted on the conveying tool 150 and placed on the placing face 20A of the XY stage 20. A drug solution is jetted from the nozzle 28 to the dummy mold and landed in the dummy mold.

Next, the XY stage 20 is moved in the X direction and the Y direction such that the landed drug solution is at the center of the angle of view of an image captured by the camera 22. Here, the moving amount of the XY stage 20 in the X direction is the distance $d_1$, and the moving amount in the Y direction is the distance $d_2$.

The filling of the drug solution is not limited to dropwise addition by the ink jet head. Slit filling using a squeegee or dropwise addition by a tiny dispenser may be used.

The XY stage 20 may be configured as an adsorption stage to hold the conveying tool 150 on the XY stage 20 by adsorption. Accordingly, flatness of the mold 120 can be kept, and thus the drug solution can be appropriately landed in the needle-like recessed portion 132.

Post-Drug Solution Filling Measurement Step (Step S3)

In the post-drug solution filling measurement step, the mass of the mold 120 after the drug solution filling step is measured. As shown in F7B of FIG. 7, a mass $W_{1A}$ of the mold 120 including the mass of the conveying tool 150 is measured by the electronic balance 10 in a state in which the mold 120 is mounted on the conveying tool 150.

The filling of the drug solution may be performed while the mass of the mold 120 is measured. Accordingly, it is possible to shorten the time for the pre-drug solution filling measurement step and the post-drug solution filling measurement step.

Drug Solution Filling Amount Determination Step (Step S4)

In the drug solution filling amount determination step, the filling amount of the drug solution in the mold 120 is determined from a difference ($W_{1A}$-$W_{1B}$) between the mass $W_{1B}$ of the mold 120 before the drug solution filling step and the mass $W_{1A}$ of the mold 120 after the drug solution filling step.

Here, in a case of $W_{1MIN} \leq (W_{1A}-W_{1B}) \leq W_{1MAX}$ (an example within a certain range), the filling amount is determined to be normal. $W_{1MIN}$ is a value determined from a minimum amount of the drug solution required for one dose of the percutaneous absorption sheet 100, and $W_{1MAX}$ is a value determined from a maximum amount of the drug solution required for one dose of the percutaneous absorption sheet 100.

In a case where the filling amount is determined to be normal, the process proceeds to Step S5. In a case of $W_{1MIN} \geq (W_{1A}-W_{1B})$ or $(W_{1A-W1B}) > W_{1MAX}$, the filling amount is determined to be abnormal, and the corresponding mold 120 is eliminated from the percutaneous absorption sheet manufacturing steps.

Drug Solution Filling State Determination Step (Step S5)

In the drug solution filling state determination step, the filling state of the drug solution in the mold 120 after the drug solution filling step is determined.

The drug solution landed in the needle-like recessed portion 132 is required to close the needle-like recessed portion 132. That is, the drug solution is required to be in contact with the needle-like recessed portion over the whole circumference of the wall portion of the needle-like recessed portion 132. In a case where the landed drug solution does not close the needle-like recessed portion 132, a tapered tip of the tip recessed portion 134 cannot be filled with the landed drug solution in a drug solution suction step to be described later. Accordingly, it is necessary to confirm the filling state of the drug solution.

Figure 10:
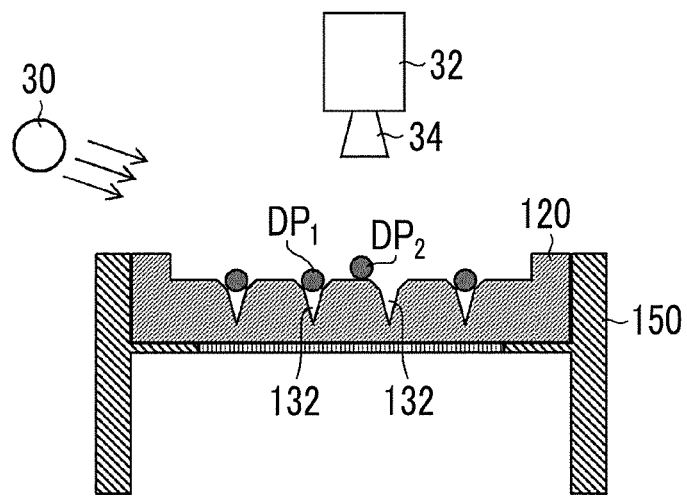
FIG. 10 is a schematic diagram showing a drug solution filling state determination step.

FIG. 10 is a schematic diagram showing the drug solution filling state determination step. In the drug solution filling state determination step, a light source 30, a camera 32, and the like are used. The light source 30 is formed of, for example, a halogen lamp or a light emitting diode (LED). The light source 30 irradiates the front face 120A of the mold 120 with visible light.

The camera 32 is provided with an imaging lens 34. The configurations of the camera 32 and the imaging lens 34 are the same as those of the camera 22 and the imaging lens 24. The camera 32 images the mold 120, and acquires a captured image of the mold 120.

In this embodiment, an image of the mold 120 captured by the camera 32 is analyzed, and, from the captured image, a drug solution droplet which has not been landed in the needle-like recessed portion 132, but been landed at a position other than the needle-like recessed portions 132 is detected to determine the filling state of the drug solution.

A liquid droplet $DP_1$ shown in FIG. 10 is an example of a liquid droplet landing in the needle-like recessed portion 132. A liquid droplet $DP_2$ is an example of a liquid droplet landing in the outside of the needle-like recessed portion 132. The liquid droplet $DP_1$ and the liquid droplet $DP_2$ are differently shaded by light applied from the light source 30. By detecting the difference in shade from the captured image, a drug solution droplet landing at a position other than the needle-like recessed portions 132 is detected.

Here, whether the drug solution droplets have landed in all the needle-like recessed portions 132 is confirmed by the presence or absence of a drug solution droplet landing at a position other than the needle-like recessed portions 132. In a case where there is no drug solution droplet landing at a position other than the needle-like recessed portions 132, it is determined that the drug solution droplets have landed in all the needle-like recessed portions 132, and the filling state of the drug solution is determined to be normal. The process proceeds to Step S6. In a case where there is a drug solution droplet landing at a position other than the needle-like recessed portions 132, it is determined there is a needle-like recessed portion 132 in which no drug solution droplet has landed, and the filling state of the drug solution is determined to be abnormal. The corresponding mold 120 is eliminated from the percutaneous absorption sheet manufacturing steps.

In some cases, no drug solution droplet landing at a position other than the needle-like recessed portions 132 exists since the drug solution has not been jetted. In this case, $W_{1MIN} > (W_{1A}-W_{1B})$ is obtained, and the filling amount of the drug solution is determined to be abnormal in the drug solution filling amount determination step.

The order of the drug solution filling amount determination step and the drug solution filling state determination step may be reversed. In addition, evaporation (drying) of the solvent of the drug solution fed in the drug solution filling step is promoted. It may be better to measure the mass of the drug solution after filling as early as possible in order to reduce the influence on the mass due to the evaporation. Therefore, the post-drug solution filling measurement step is preferably performed before the drug solution filling state determination step.

First Suction Step (Step S6)

In the first suction step, the mold 120 determined to be normal in the drug solution filling amount determination step and the drug solution filling state determination step is sucked from the rear face 120B. FIG. 11 is a schematic diagram showing the first suction step. In the first suction step, an adsorption plate 40 or the like is used.

First, as shown in F11A of FIG. 11, the mold 120 mounted on the conveying tool 150 is placed on the adsorption plate 40. The adsorption plate 40 is formed of, for example, a porous member. Examples of the porous member include a metal sintered body, a resin, and ceramics.

The adsorption plate 40 is connected to a vacuum pump (not shown). Air suction is possible from a surface of the adsorption plate 40 by driving the vacuum pump. Accordingly, the mold 120 is sucked from the rear face 120B via the ventilation portion 154 of the seating face 152 of the conveying tool 150.

As a result of the suction, the drug solution landed in the needle-like recessed portions 132 of the mold 120 flows into the tapered tips of the needle-like recessed portions 132 as shown in F11B of FIG. 11. Therefore, it is possible to concentrate the active ingredient of the drug solution at the tip of the needle portion 114 of the percutaneous absorption sheet 100.

Drug Solution Evaporation And Drying Step (Step S7)

Figure 12:
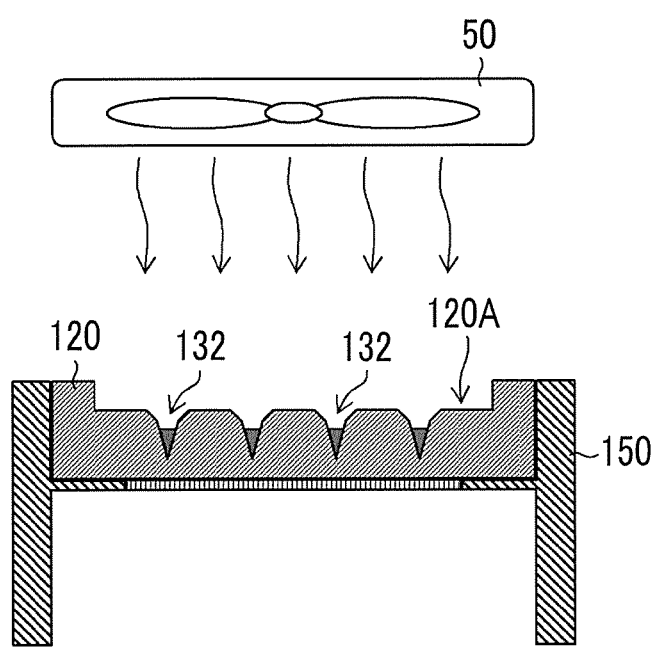
FIG. 12 is a schematic diagram showing a drug solution evaporation and drying step.

In the drug solution evaporation and drying step, the solvent of the drug solution is evaporated and dried after the first suction step. FIG. 12 is a schematic diagram showing the drug solution evaporation and drying step. In the drug solution evaporation and drying step, a blower fan 50 or the like is used.

The blower fan 50 blows air to the front face 120A of the mold 120, thereby drying the drug solution filling the needle-like recessed portions 132 by blowing. Drying by heating or drying under reduced pressure may be performed.

Pre-Base Solution Filling Measurement Step (Step S8)

Figure 13:
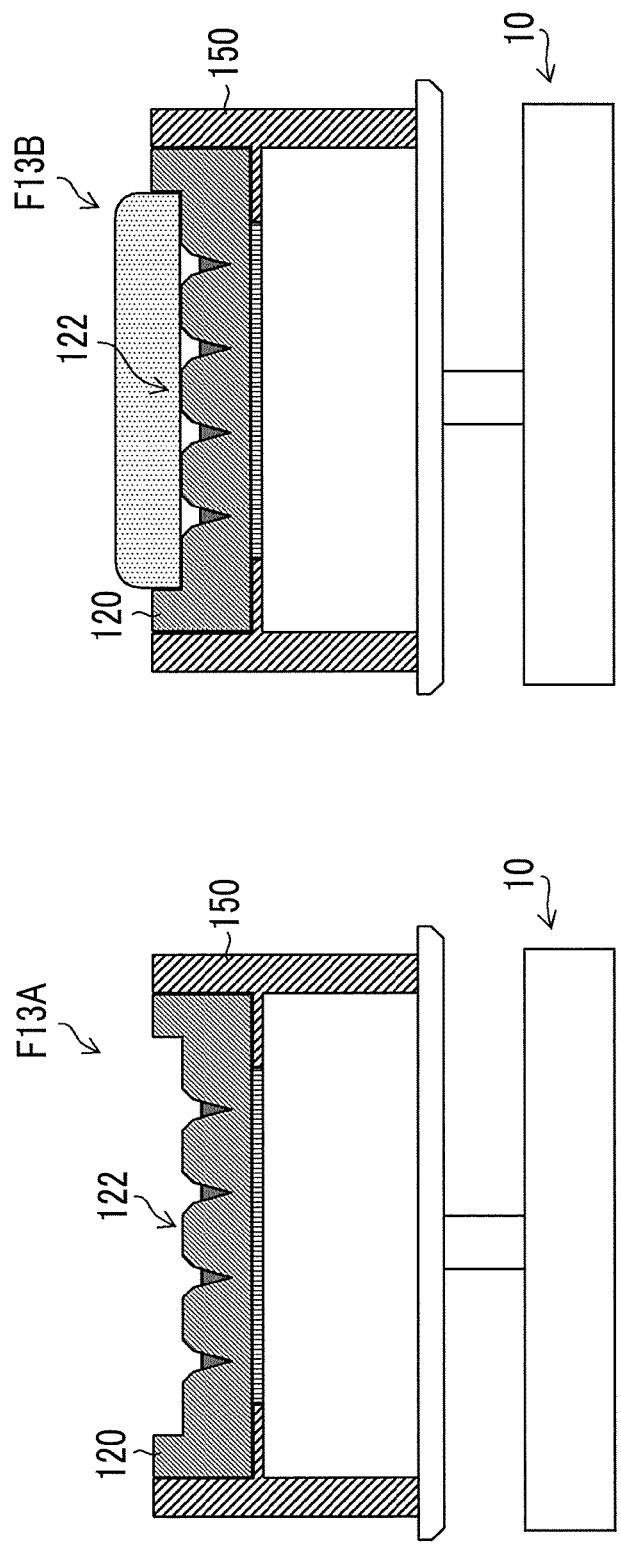
FIG. 13 is a schematic diagram showing a pre-base solution filling measurement step and a post-base solution filling measurement step.

In the pre-base solution filling measurement step, the mass of the mold 120 before the base solution filling step is measured. FIG. 13 is a schematic diagram showing the pre-base solution filling measurement step and the post-base solution filling measurement step. As shown in FIG. 13, in the pre-base solution filling measurement step and the post-base solution filling measurement step, the electronic balance 10 is used as in the pre-drug solution filling measurement step and the post-drug solution filling measurement step.

As shown in F13A of FIG. 13, in the pre-base solution filling measurement step, a mass $W_{2B}$ of the mold 120 including the mass of the conveying tool 150 is measured in a state in which the mold 120 is mounted on the conveying tool 150.

Base Solution Filling Step (Step S9)

In the base solution filling step, the needle-like recessed portions 132 of the mold 120 are filled with a base solution. The base solution is a drug-free polymer solution, and as a water-soluble polymer substance forming the polymer solution, a water-soluble polymer substance such as chondroitin sulfate, hydroxyethyl starch, or dextran is preferably used.

Figure 14:
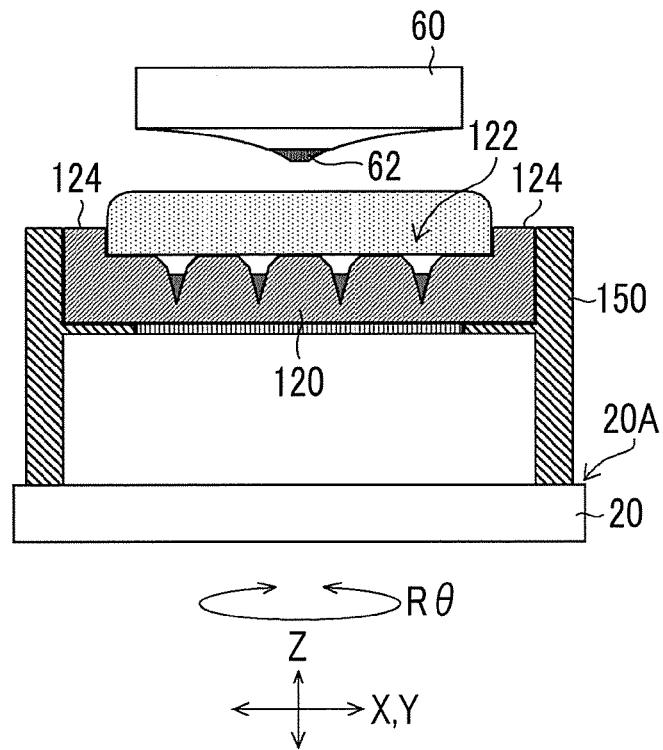
FIG. 14 is a schematic diagram showing a base solution filling step.

FIG. 14 is a schematic diagram showing the base solution filling step. In the base solution filling step, the XY stage 20, a base solution spotting head 60, and the like are used. The base solution spotting head 60 has a nozzle 62 (an example of a base solution spotting nozzle) through which a base solution is discharged.

First, as in the drug solution filling step, the position of the needle-like recessed portion 132 of the mold 120 placed on the XY stage 20 in the XY plane and the position of the nozzle 62 of the base solution spotting head 60 in the XY plane are adjusted. Next, based on the result of the positional adjustment, the XY stage 20 is controlled to move the mold 120 in the X direction and the Y direction, and thus the base solution spotting head 60 and the mold 120 are positionally adjusted.

Then, a certain amount of the base solution is held while flowing out of the nozzle 62 of the base solution spotting head 60, and the held base solution is brought into contact with the flat portion 122 surrounded by the bank portion 124 of the mold 120 to spot the held base solution for filling.

The filling of the base solution is not limited to spotting by the spotting head, and dropwise addition by a dispenser may be performed.

Post-Base Solution Filling Measurement Step (Step S10)

In the post-base solution filling measurement step, the mass of the mold 120 after the base solution filling step is measured. As shown in F13B of FIG. 13, in the post-base solution filling measurement step, a mass $W_{2A}$ of the mold 120 including the mass of the conveying tool 150 is measured in a state in which the mold 120 is mounted on the conveying tool 150.

The filling of the base solution may be performed while the mass of the mold 120 is measured. Accordingly, it is possible to shorten the time for the pre-base solution filling measurement step and the post-base solution filling measurement step.

Base Solution Filling Amount Determination Step (Step S11)

In the base solution filling amount determination step, the filling amount of the base solution in the mold 120 is determined from a difference ($W_{2A}$-$W_{2B}$) between the mass $W_{2B}$ of the mold 120 before the base solution filling step and the mass $W_{2A}$ of the mold 120 after the base solution filling step.

Here, in a case of $W_{2MIN} \leq (W_{2A}-W_{2B}) \leq W_{2MAX}$ (an example within a certain range), the filling amount is determined to be normal. $W_{2MIN}$ is a value determined from a minimum amount of the base solution required for one dose of the percutaneous absorption sheet 100, and $W_{2MAX}$ is a value determined from a maximum amount of the base solution required for one dose of the percutaneous absorption sheet 100.

In a case where the filling amount is determined to be nominal, the process proceeds to Step S12. In a case of $W_{2MIN} > (W_{2A}-W_{2B})$ or $(W_{2A}-W_{2B}) > W_{2MAX}$, the filling amount is determined to be abnormal, and the corresponding mold 120 is eliminated from the percutaneous absorption sheet manufacturing steps.

Base Solution Filling State Determination Step (Step S12)

Figure 15:
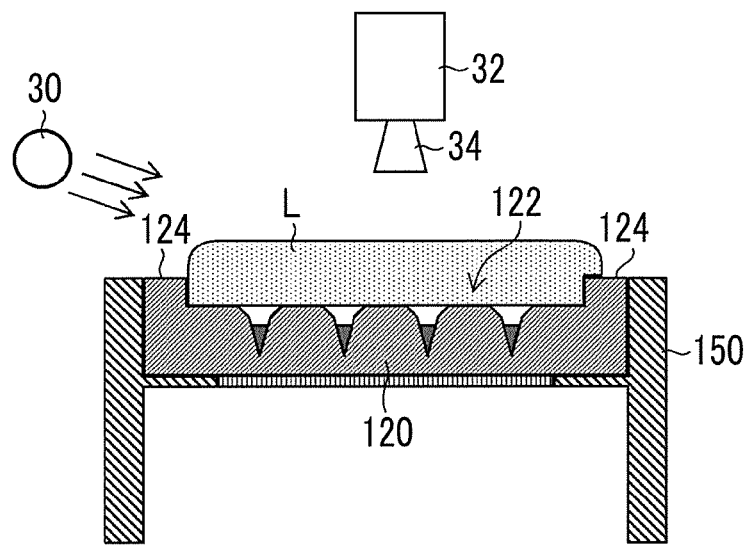
FIG. 15 is a schematic diagram showing a base solution filling state determination step.

In the base solution filling state determination step, the filling state of the base solution in the mold 120 after the base solution filling step is determined. FIG. 15 is a schematic diagram showing the base solution filling state determination step. In the base solution filling state determination step, the light source 30, the camera 32, and the like are used as in the drug solution filling state determination step.

The base solution is required to be supplied only to the flat portion 122 (an example of a region surrounded by the bank portion) of the mold 120. In this embodiment, an image of the mold 120 captured by the camera 32 is analyzed, and, from the captured image, a base solution protruding to the bank portion 124 is detected to determine the filling state of the base solution.

In a case where the base solution exists only in the flat portion 122, the filling state of the base solution is determined to be normal, and the process proceeds to Step S13. In a case where the base solution exists in the bank portion 124, the filling state of the base solution is determined to be abnormal, and the corresponding mold 120 is eliminated from the percutaneous absorption sheet manufacturing steps.

A base solution L shown in FIG. 15 is an example of the base solution protruding to the bank portion 124.

Second Suction Step (Step S13)

In the second suction step, the mold 120 determined to be normal in the base solution filling amount determination step and the base solution filling state determination step is sucked from the rear face 120B. FIG. 16 is a schematic diagram showing the second suction step. In the second suction step, the adsorption plate 40 or the like is used as in the first suction step.

First, as shown in Fl6A of FIG. 16, the mold 120 mounted on the conveying tool 150 is placed on the adsorption plate 40. A vacuum pump (not shown) connected to the adsorption plate 40 is driven to perform air suction from a surface of the adsorption plate 40. Accordingly, the mold 120 is sucked from the rear face 120B via the ventilation portion 154 of the seating face 152 of the conveying tool 150.

As a result of the suction, the base solution filling the flat portion 122 of the mold 120 flows into the needle-like recessed portions 132 as shown in Fl6B of FIG. 16.

Base Solution Evaporation And Drying Step (Step S14)

Figure 17:
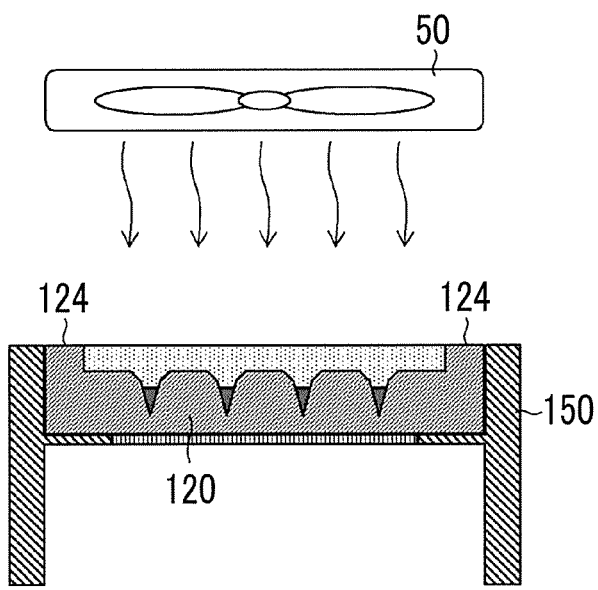
FIG. 17 is a schematic diagram showing a base solution evaporation and drying step.

In the base solution evaporation and drying step, the solvent of the base solution is evaporated and dried after the second suction step. FIG. 17 is a schematic diagram showing the base solution evaporation and drying step. In the base solution evaporation and drying step, the blower fan 50 or the like is used as in the drug solution evaporation and drying step.

The blower fan 50 blows air to the front face 120A of the mold 120, thereby drying the base solution filling the flat portion 122 by blowing. Drying by heating or drying under reduced pressure may be performed.

Releasing Step (Step S15)

Figure 18:
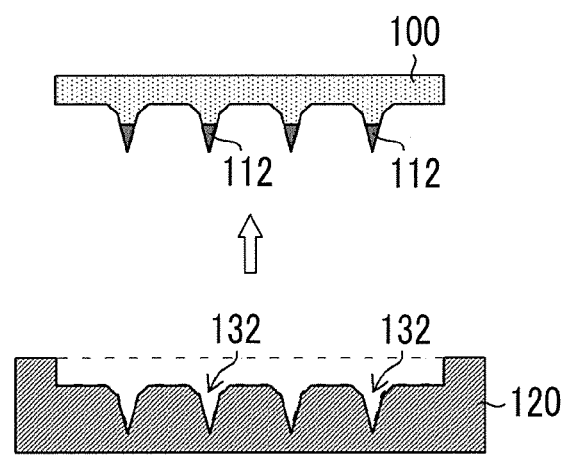
FIG. 18 is a schematic diagram showing a releasing step.

In the releasing step, the sheet (percutaneous absorption sheet 100) formed through the base solution evaporation and drying step is released from the mold 120. FIG. 18 is a schematic diagram showing the releasing step.

As described above, in a case where the mass of the mold 120 is measured before and after filling of the needle-like recessed portions 132 of the mold 120 for manufacturing one dose of the percutaneous absorption sheet 100 with a liquid, and the filling amount of the liquid is determined from a difference in mass of the mold 120 before and after the filling of the liquid, the filling amount of the liquid in the mold can be guaranteed. Accordingly, the active ingredient content of the percutaneous absorption sheet 100 can be guaranteed.

In addition, in a case where the filling state of the liquid in the mold 120 after the filling of the liquid is determined, and the mold 120 having a good filling state is sucked from the rear face, the active ingredient of the liquid can be concentrated at the tips of the needle-like recessed portions 132. Accordingly, the active ingredient can be concentrated at tips of the needle-like protruding portions 112 of the percutaneous absorption sheet 100.

EXPLANATION OF REFERENCES

10: electronic balance
20: XY stage
20A: placing face
22: camera
24: imaging lens
26: drug solution jetting head
28: nozzle
30: light source
32: camera
34: imaging lens
40: adsorption plate
50: blower fan
60: base solution spotting head
62: nozzle
100: percutaneous absorption sheet
100A: front face
100B: rear face
102: sheet portion
110: protrusion pattern
112: needle-like protruding portion
114: needle portion
116: frustum portion
120: mold
120A: front face
120B: rear face
122: flat portion
124: bank portion
130: recess pattern
132: needle-like recessed portion
134: tip recessed portion
136: cup portion
150: conveying tool
152: seating face
154: ventilation portion
$DP_1$: liquid droplet
$DP_2$: liquid droplet
L: base solution
S1 to S15: steps in method of manufacturing percutaneous absorption sheet
S21 to S24: steps in drug solution filling step

What is claimed is:

1. A method of manufacturing a microneedle array in which a plurality of needle-like recessed portions of a surface of a mold are filled with a liquid to form one dose of a patch having a plurality of needle-like protruding portions on a surface thereof, the method comprising:
   a pre-filling measurement step of measuring a mass of the mold;
   a filling step of filling the needle-like recessed portions of the mold whose mass is measured with the liquid;
   a post-filling measurement step of measuring a mass of the mold filled with the liquid;
   a filling amount determination step of determining a filling amount of the liquid from a difference in mass of the mold before and after the filling of the liquid;
   a filling state determination step of determining a filling state of the liquid in the mold filled with the liquid;
   a suction step of sucking the mold in which the filling amount and the filling state of the liquid are determined to be normal from a rear face; and
   an evaporation and drying step of evaporating and drying a solvent of the liquid of the sucked mold.

2. The method of manufacturing a microneedle array according to claim 1,
   wherein in the filling amount determination step, the filling amount is determined to be normal in a case where the difference is within a certain range.

3. The method of manufacturing a microneedle array according to claim 1,
   wherein the liquid is a drug solution containing a drug, and
   in the filling step, a position of the mold is made to coincide with a position of a drug solution jetting nozzle, and the drug solution is jetted from the drug solution jetting nozzle to be landed in the needle-like recessed portions.

4. The method of manufacturing a microneedle array according to claim 3,
   wherein the filling step includes
   a step of imaging a plurality of positions in the mold, and
   a step of calculating positions of the needle-like recessed portions based on the imaged plurality of positions.

5. The method of manufacturing a microneedle array according to claim 3,
   wherein in the filling state determination step, a captured image of the mold filled with the liquid is analyzed, and the filling state of the drug solution is determined to be normal in a case where the drug solution lands in all the needle-like recessed portions of the mold.

6. The method of manufacturing a microneedle array according to claim 3,
wherein the liquid is a base solution, and
in the filling step, a position of the mold is made to coincide with a position of a base solution spotting nozzle, and the needle-like recessed portion in which the drug solution filling the recessed portion is evaporated and dried is filled with the base solution by spotting.

7. The method of manufacturing a microneedle array according to claim 6,
wherein the mold has a thick bank portion at a peripheral portion thereof, and
in the filling state determination step, a captured image of the mold after the filling of the base solution is analyzed, and the filling state of the base solution is determined to be normal in a case where the base solution exists only in a region surrounded by the bank portion.

8. The method of manufacturing a microneedle array according to claim 1,
wherein the post-filling measurement step is performed before the filling state determination step.

9. The method of manufacturing a microneedle array according to claim 1,
wherein the mold is placed on a conveying tool, and
in the pre-filling measurement step and the post-filling measurement step, a mass of the conveying tool and the mold is measured.

10. The method of manufacturing a microneedle array according to claim 9,
wherein the conveying tool is provided with adsorption holes in a seating face on which the mold is placed.

11. The method of manufacturing a microneedle array according to claim 1,
wherein the mold has gas permeability.

* * * * *